United States Patent [19]

Brehm et al.

[11] Patent Number: 4,897,225

[45] Date of Patent: Jan. 30, 1990

[54] PROCESS FOR THE PREPARATION OF ROOM TEMPERATURE FLOWABLE DERIVATIVES OF NATURAL FATS AND OILS AND THEIR USE

[75] Inventors: Helmut Brehm; Helmut Klimmek; Dolf Stockhausen, all of Krefeld, Fed. Rep. of Germany

[73] Assignee: Chemische Fabrik Stockhausen GmbH, Krefeld, Fed. Rep. of Germany

[21] Appl. No.: 53,299

[22] Filed: May 22, 1987

[30] Foreign Application Priority Data

May 26, 1986 [DE] Fed. Rep. of Germany ....... 3617657

[51] Int. Cl.[4] .......... C07C 143/90

[52] U.S. Cl. .......... 260/400; 8/94.22

[58] Field of Search .......... 260/400

[56] References Cited

U.S. PATENT DOCUMENTS 3,891,689 6/1975 Pryce .......... 260/400

FOREIGN PATENT DOCUMENTS 0247509 12/1987 European Pat. Off. .......... 260/400

1198815 8/1965 Fed. Rep. of Germany .

*Primary Examiner*—Anton H. Sutto

*Attorney, Agent, or Firm*—Sprung Horn Kramer & Woods

[57] ABSTRACT

The present invention relates to a process for the production of derivatives of natural fats and oils that is characterized in that the fats that are solid at room temperature or which contain solid fractions, mixtures of these with free fatty acids, mono- and/or diglycerides are oxyalkylated at elevated temperatures in the presence of basic catalysts having at least one 1,2-epoxide and the conversion products so obtained, optionally, after epoxidization are sulphonated in a manner known per se. The products are particularly suitable for use as leather dubbing agents.

13 Claims, No Drawings

PROCESS FOR THE PREPARATION OF ROOM TEMPERATURE FLOWABLE DERIVATIVES OF NATURAL FATS AND OILS AND THEIR USE

The present invention relates to a process for the production of derivatives of natural fats and oils that are liquid or free-flowing, respectively, at room temperature and their use in leather dubbing.

Natural fats and oils of vegetable and animal origin are mainly used for human nutrition. However, ever greater quantities of these fats and oils are being used as secondary materials in the most varied branches of industry. In this connection, the technological utility of these products depends specifically on the particular properties of the fats and oils. In their turn, these are determined mainly by their composition and molecular structure. In the main, natural fats and oils are composed of triglycerides (neutral fats) and—to a lesser extent—of phosphorlipids and free fatty acids. The properties of this group of substances—and this applies particularly to the neutral fats—are determined by the type of the fatty acids bound to the glycerine molecule, i.e., with regard to the chain length (short, medium, and long chain), by their degree of saturation and conformation (saturated, mono-unsaturated or polyunsaturated; cis-, trans-arrangement), and by the arrangement and quantity per glycerine molecule.

Taken all in all, this means that, in the final analysis, the particular structure of the components of the natural fats and oils determine and very frequently limit their technological utility to a very great extent if no changes can be or are made to the molecule—whether because such changes are counter-indicated on the basis of cost or because the desired modifications cannot be made conventionally by normal chemical practice.

Based on technologies used to date, natural fats and oils must be subjected to specific cleaning processes or separation, respectively, in the solid and the liquid phases or else undergo hardening. Ultimately, the desired "fat chemicals" result from the separation or conversion products of the natural oils and fats i.e. fatty acids, glycerine and fatty acid methol esters (the actual basic oleochemical raw materials) and the fatty alcohols and fatty amines that are important because of this significance for the most diverse derivatives.

Since the molecular structure of natural fats and oils is determined by their origin, fats and oils per se are for all practical purposes unuseable "fatty chemicals," and for this reason "tailored" fats and oils must be produced by means of industrial processes. The processes required for this are characterized by the consumption of large amounts of energy and high investment costs. In addition, they are frequently of low-level specificity i.e. they give rise to the danger of isomerisation of the fatty acids, production of mixtures instead of unified products).

Using examples taken from the leather production-agents industry, it will be apparent that technological utility in keeping with specific demands is only possible with specific dubbing compositions. With regard to the technological workability of fats, it is important that these be in a free-flowing form. Animal carcass fats, the use of which is desirable in the production of dubbing agents, are solid. In order to render these useful, they must be liquified. This can take place by fractionation. However, this process is costly, uses large quantities of energy, and is relatively costly. In the search for the cheapest possible substitute fats that are available in large quantity, their industrial suitability is diminished by the fact that in most instances these are fats in solid form and these, too, have to be liquified in a suitable process. Fats and oils that are of high viscosity permit only superficial dubbing of leather, so that there is a danger of fat spotting on leather that is so treated. A qualitatively high quality leather must be dubbed with low-viscosity fat and this, too, requires the adjustment of a specific viscosity. For the technological subsequent treatment of fats for leather dubbing, it is frequently required that there be double bonds in the fatty acid molecules (e.g., for the completion of sulphonation). Up to now, raw products of this kind have been available only in natural oils that are, moreover, relatively costly. On the other hand, many unsaturated, correspondingly thin-bodied oils are undesirable for use in leather dubbing, because there is a danger of resinification due to the high content of unsaturated double bonds.

For the above-cited technical reasons, sperm oil (a liquid product) was for many years the choice of the leather-processing industry. Sperm oil makes finished leather exceptionally pliable and has been used for many years in the production of very high quality leather. Furthermore, the properties of leather of inferior quality can be so improved by treatment with sperm oil that it can satisfy even the highest demands for quality.

As a consequence of efforts made to protect the sperm whale—the source of sperm oil—the use of sperm oil had been stopped in Europe to avoid extermination of the species. Synthetically produced triolein as well as lard oil (the liquid phase of lard) have been used as replacement products for sperm oil—particularly in the leather industry. Dubbing is usually carried out in oil water emulsions with the help of leather oils.

Leather oils are self-emulsifying products composed of a neutral oil fraction and an emulsifier fraction. Depending on their charge character, they provide anionic, cationic, amphoteric and non-ionic dubbing agents. Very frequently, distinction is also drawn between synthetic and native fat-liquors, with the distinction between the two becoming increasingly blurred. The emulsifier fraction is either produced for the greater part in neutral oil by partial sulphonation, for example, or else is added thereto as a separate component.

Sulphonated and sulfited native oils and fats contain alpha-sulfo-fatty acids and hydroxysulfonates. Alkane-, alpha-olefin-, dialkylbenzol- and chloroparafin sulphonates as well as long chain fatty alcohol sulphonates, phosphoric acid, citric acid, and alkylsuccinic acid esters are found in synthetic fat liquors.

The emulsifying, mostly polar fractions of a dubbing agent are for the most part bonded by the leather, predominantly in the form of ionic linkages or by the formulation of stable metal complexes in a non-extractable and non-migratable form.

The linking of the emulsified fractions takes place by van der Waal forces through polar groups. The emulsifying fractions influence the linking of the emulsified fractions insofar as they are responsible for their distribution within the leather and thus exert an anchoring effect by intermolecular forces.

Dubbing is a process that determines the quality in the production of leather. This is especially applicable to very soft types of leather. The following characteristics of leather are very greatly influenced by dubbing:

softness; mechanical properties such as resistance to wear and to tearing, stretch, grain elasticity, etc.; fullness, grain consistency and feel; the characteristics of the surface of the leather for subsequent finishing processes.

It is known that softness is based mainly on separation of the fibre bundles and fibriles during the drying process. Accordingly, the ability of a dubbing agent to so alter the surface of the fibres and the fibriles that no adhesion takes place during drying is an essential criteria for the softening properties of a dubbing agent. This property is greatly affected by the emulsifying fractions of the dubbing agent. The lubricating effect of the emulsified fractions of a fat-liquor plays a decisive role with regard to the elastic properties, such as tensile strength, stretch and grain elasticity. The fibres that have been "coated" with a lubricating agent have a greater ability to slide and thus, at the same time, exhibit reduced internal friction.

It is to be assumed that a marked spreadability of the emulsified fractions has a decisive effect on their lubricating effect. To clarify this, reference is made to the fact that spreadability is understood to be the property of a substance to spread over the surface of a solid or liquid substance in a mono-molecular layer. The greater the spreadability, the smaller the quantity of substance required in each instance. Unfortunately, up to now there has been a lack of test data concerning the effect of varying spreadability of the emulsified fractions of a dubbing agent on the dubbing effect. One reason for this is the costly and complicated measuring technique that is involved. Furthermore, there is the fact that the emulsified fraction of a fat liquor can have a decisive effect on the spreadability of the emulsified fractions.

The practitioner is familiar with the fact that the quantity and type of the dubbing agent affect the fullness, grain consistency and the feel of the leather. As far as the filling effect is concerned, assessment of this is almost always based on subjective observations. In special cases, however, fullness can be determined objectively by measuring the increase in thickness of the leather.

The filling effect of dubbing agents is particularly evident in the case of thin leather types up to a maximum thickness of approximately 1.2 mm (for cattle hides). It is possible, by proper selection and, optionally, increased use of the product, to reduce the normally required amount of retanning material or even dispense with retanning altogether.

In the case of soft leather types that are more than 1.2 mm thick, it is often difficult to achieve good grain consistency. The main reason for a "loose grain" is the variable histological structure of the grain layer—the papillary layer on the one hand, and the reticular layer on the other.

Very often, however, the "loose grain" is caused by incorrect selection of the dubbing agent or an unsuitable dubbing technique. In order to avoid this fault in the leather, which reduces its quality, one has to strive for a fat distribution over the cross-section of the leather, which ensures that the mechanical properties, in particular the softness of the grain and the reticular layer, are roughly uniform in the critical boundary area between the two layers.

Ultimately, the "hand" of the leather is also dependent on the type, quantity, and characteristics of the dubbing agent used. This cannot be measured objectively and is extremely difficult to define. Softness and grain consistency are only parts of what the expert understands by this term. There is, for example, a "round" hand or a "solid" hand, and only the specialist is any position to assess the hand of a leather correctly.

The physical properties of the surface of the leather for subsequent finishing are influenced decisely by the structure of the dubbing agent that is used. This applies, above all else, to the absorbency of the surface of the leather, which is so important for modern finishing methods. It has already been explained that conventional fat-liquor dubbing sgents consist of an emulsifier and an emulsified fraction. It is the emulsifying components that are responsible for the behaviour of the surface of the leather for subsequent processes. These determine the hydrophyllic or hydrophobic character of the leather. Additionally, their ionic behaviour influences the electrical charge present on the surface.

It is an object of the present invention to use as starting material fatty raw materials such as animal carcass fats, containing solids or solid fractions, which are available in large quantities and for this reason are favourably priced, to convert these in an energy-efficient manner into derivatives which, in addition to having a dubbing effect, simultaneously have an emulsifying action and a high spreadability and which, for this reason, are particularly suitable as dubbing agents for leather.

Thus, according to the present invention, there is provided a process for the production of derivatives of natural fats and oils that are liquid or free-flowing at room temperature, respectively, and their use in leather dubbing, characterized in that fats that are solid at room temperature or contain solid fractions, mixtures of these with free fatty acids, mono- and/or diglycerides are oxyalkylated at elevated temperatures in the presence of basic catalysts with at least one 1,2-epoxide, and the conversion product so obtained is sulphonated, optionally after epoxydation, in a known manner.

Oxylalkylation is a well-known reaction. The mechanism of oxyalkation of a triglyceride that is practically free of active hydrogen atoms—i.e., which are capable of reacting relative to alkylene oxides—is discussed in *Tenside* 3 (1966, volume 2, page 37). DE-AS 12 70 542 describes the conversion of fats that are respectively solid and liquid at room temperature with alkylene oxides, with the aim of modifying the surface-active properties of the fat to provide washing agents, defoamers, emulsifying agents, and the like.

Surprisingly, the animal and/or vegetable fats used according to the present invention, which are solid or contain solid fractions, respectively, at room temperature, not only retain the dubbing character of the oxyalkation product, but the industrial application properties of these products as leather-processing agents are even improved if the fats that have been converted with alkylene oxide are still sulfited or sulphonated. The products so obtained display dubbing properties that are at least equal to those of products based on fats which are liquid at room temperature—such as, for example, neat's foot oil or lard oil.

Dubbing according to the present invention is obtained by the alkoxylation that precedes the sulphonation process and this dubbing provides completely unified emulsions that are very productive, which are superior to conventional dubbing agents with added emulsifier (the expression "sulphation" is here understood to be a common generic term for the introduction of sulphate groups and sulphonic acid groups that are introduced either by treatment with concentrated sulfuric acid or by oxidizing sulfitation in the fat molecule).

Fundamentally, all triglycerides and their mixtures formed with free fatty acids, mono- and/or diglycerides are numbered amongst the fats that can be used as starting materials according to the present invention. Of particular practical importance is the conversion of fats or oils, respectively, with a turbidity point above that of lard oil.

The following Table 1 indicates the gas chromatographically determined composition of two examples of fats to be used according to the present invention (Fat 1 and Fat 2 in comparison to lard oil):

TABLE 1

| C-Distribution | According to present invention Fat 1 (%) | Fat 2 (%) | Comparison lard oil (%) |
|---|---|---|---|
| $C_{14}$ | 1,5 | 2,5 | 1,5 |
| $C_{14:1}$ | — | 1,5 | |
| *$C_{15}$ | 0,5 | 0,5 | 0,5 |
| $C_{16}$ | 26,5 | 26,0 | 23 |
| $C_{16:1}$ | 3,0 | 9,5 | 3,5 |
| *$C_{17}$ | 1,0 | 1,0 | 0,5 |
| $C_{18}$ | 28,5 | 3,0 | 2,5 |
| $C_{18:1}$ | 31,0 | 52,0 | 56 |
| $C_{18:2}$ | 4,5 | 2,0 | 9,0 |
| $C_{18:3}$ | 0,5 | 1,0 | 0,5 |
| *$C_{19}$ | 0,5 | 0,5 | 0,5 |
| $C_{20}$ | 2,0 | 0,5 | 2,0 |
| *$C_{22}$ | 0,5 | — | |
| Solidification point (°C.): | 24 | 23 | |
| Turbidity point (°C.): | — | — | 10 |

*With unsaturated fractions

It is not absolutely necessary to use fats of a specific origin, but, for example, Fat 1 and Fat 2 from Table 1 can be used in admixture. Or, for example, it is possible to use mixtures of bone fat and skin fat.

The useable fats can also be partially split, so that in addition to mono- and diglycerides there are also free fatty acids. The acid number of the fat is not critical, as has been shown by oxylalkation experiments involving the addition of free fatty acids.

Oxylalkylation can take place in the presence of small quantities of water as occur in natural fats, or by aqueous catalyst dissolution.

Ethylene oxide, propylene oxide, butylene oxide, styrene oxide, 1,2-epoxybutadiene, 1,2-epoxycyclohexene may be used as 1,2-epoxides. If more than one epoxide is used, then these can be converted successively or as a mixture with the fats. Propylene oxide is preferred for the oxyalkation.

Basic compounds such as sodium and potassium hydroxide in solid form or as aqueous solutions, sodium methylate, or the alkaline salts of fatty acids are used as catalysts for the conversion of the alkylene oxides with the fats, in which connection postassium hydroxide is preferred.

Conversion takes place by a known process at an elevated temperature. In order to arrive at a rapid reaction of the alkylene oxide, a reaction temperature in the range from 150° to 170° C., e.g., of 160° C., has been shown to be expedient.

Depending on the consistency of the fat, 5 to 100%-wt of alkylene oxide and preferably 10 to 25%-wt alkylene oxide, relative to the quantity of fat, is added. The alkoxylation is preferably carried out at a normal pressure of up to 10 bar. If the alkoxylation is carried out with a plurality of 1,2-epoxides, the epoxides can either be converted one after the other with the starting fats, or the conversion can be carried out with a mixture of the epoxides. If conversion is carried out with more than one 1,2-epoxide, then it is preferred that propylene oxide and ethylene oxide be used.

Subsequent to the alkoxylation, the oxalkylated fats are sulphated by a known method. The sulphation can be carried out with concentrated sulfuric acid at room temperature up to slightly increased temperatures (from approximately 30° C.) for a few hours.

The quantity of concentrated sulfuric acid amounts advantageously to 15 to 35, and preferably 20 to 30%-wt, relative to the oxyalkation product. Alternatively, sulfonic acid groups can be introduced by treatment with sodium disulfite in the presence of atmospheric oxygen. After the sulphation or sulfitation, the product so obtained is adjusted to a pH value in the vicinity of the neutral point (e.g., pH 6.5). For sulphation, the alkoxylated fats obtained in the first step of the process can be mixed with hydrocarbons and/or further unsaturated fats or fatty components such as, for example, olein.

The sulphonation can be carried out immediately after the oxyalkation, in which connection the oxalkylated products do not need to be isolated. According to a further embodiment of the invention, the oxalkylated fats are epoxidized priaor to sulphonation. This can take place in a known manner, e.g., sith hydrogen peroxide in the presence of formic acid.

It is preferred that the sulphonation be carried out with an $SO_3$/air mixture with a content of up to 8%-volume $SO_3$ at temperatures of 20°-50° C.

It is advantageous that the oxalkylated products be freed of volatile components (e.g., by distillation, optionally in a vacuum).

The major advantage of the process according to the present invention lies in the fact that low quality, dark coloured fats that are normally characterized by an increased fraction of free fatty acids, e.g., 5 to 15%, can be used. Despite this, relatively light coloured, low-odour products are obtained.

EXAMPLE 1

20 g of 45% potassium hydroxide solution were added to 2000 g of bone fat with an acid number=27; iodine number=54; saponification number=198; and solidification point=25° C. contained in an autoclave stirrer, and carefully washed with nitrogen. After heating to 160° C., 354 g of propylene oxide was added little by little so as to retain the reactor temperature in the range of 155° to 165° C. and so that the pressure of 4 bar was not exceeded. Prior to each renewed addition of epoxide the reaction was allowed to settle down, which could be noted by a drop in pressure from the normal. The time required for the gradual addition of the monomer amounted to 1.5 hours. Subsequently, the reaction was allowed to continue for 30 minutes at 160° C. and the reaction mixture was stripped to remove the easily evaporated fractions. After neutralization at approximately 40° C. with concentrated sulfuric acid, oil which was slightly cloudy at 20° C. and which solidified at approximately 11° C. was extracted. Iodine number=48.7.

EXAMPLE 2

40 g of 30% sodium methylate solution was added to 200 g of dark brown animal carcass fat of low quality with an acid number=10; iodine number=55; saponification number=198; and solidification point=23° C. in a temperature controlled autoclave stirrer and then freed of oxygen and volatile fractions during heating to 120° C. by alternating evacuation to approximately 20 mbar and ventilation with nitrogen. At an internal reactor temperature of 160° C., 354 g of propylene oxide was added as described in Example 1. After neutralization of the reaction mixture with concentrated acetic acid, an opal-coloured oil that solidifies at approximately 12° C. was extracted.

EXAMPLE 3

Beef tallow (acid number=2.0; iodine number=45; saponification number=198; solidification point=34° C.) was processed as described in Example 1, but with the addition of 25%-wt of propylene oxide. After neutralization with p-toluol sulfonic acid, an oil that is cloudy at 20° C. was obtained.

EXAMPLE 4

354 g of propylene oxide was added to 2000 g of animal carcass fat (water content=0.58%; solidification point=23° C.; acid number=10; saponification number=197; iodine number=54.6) as was done in Example 1. After completion of the reaction—recognizable by the constant pressure within the reactor—176 g of ethylene oxide was added little by little at 155° to 160° C. and at a maximum reaction pressure of 4 bar. After completion of the reaction the easily evaporated fractions were removed by a vacuum of approximately 20 mbar, when the reaction product was cooled to approximately 40° C. and neutralized with sulfuric acid.

| | |
|---|---|
| Appearance at 20° C.: | a light coloured, slightly cloudy oil |
| pH value | 4.8 |
| acid number | 3.6 |
| OH number | 49.4 |
| iodine number | 43.6 |
| saponification number | 159 |
| viscosity | 780 mPas (25° C.) |

EXAMPLE 5

Animal carcass fat as in Example 4 is converted with propylene oxide and ethylene oxide as in Example 4, but with the difference that the alkylene oxides are not dosed in one after the other but are added to the reactor as a mixture, little by little. After processing, an oil that is slightly turbid at 20° C. is obtained.

| | |
|---|---|
| acid number | 4.2 |
| OH number | 50.2 |
| iodine number | 43.4 |
| saponification number | 158 |
| viscosity | 910 mPas (25° C.) |

EXAMPLE 6

20 g of 45% potassium hydroxide solution was added to 2000 g of the fat used in Example 1 in a pressure reactor. During heating this was carefully washed with the highest purity nitrogen. 354 g of ethylene oxide was added little by little at a temperature of 160° C., in order that the reaction temperature could be maintained and a pressure of a maximum of 6 bar was not exceeded. After reaction of the epoxide, the batch was cooled and the pH adjusted to 5 with sulfuric acid. A yellow cloudy oil was obtained.

| | |
|---|---|
| acid number | 4.2 |
| OH number | 51.2 |
| saponification number | 166.6 |
| viscosity | 85 mPas (25° C.) |
| iodine number | 45.5 |

EXAMPLE 7

1000 g of the reaction product obtained as in Example 1 was sulphonated at approximately 30° C. with 300 g of concentrated sulfuric acid for 5 hours. After neutralization with 30% sodium hydroxide solution to a pH value of 6.5 the salt water was separated and a liquid red-brown clear sulphonate was obtained. The content of organically formed $SO_3$=5.1%.

Chrome tanned, dyed shoe upper leather of approximately 2 mm shaved thickness from cattle hides, retanned with vegetable, synthetic and resin tanning agent was liquored at 50° C. for 45 minutes with 100% float and 7% of the product obtained (relative to the hide weight). The leather was dyed in the usual way and finished. A very soft leather with a high degree of grain consistency and of even colour was obtained.

EXAMPLE 8

A mixture of 700 g of reaction product from Example 2 and 300 g of a hydrocarbon mixture of chain length $C_{10}$ to $C_{30}$ was oxidized at 90°-120° C. with air until the decrease in the iodine number amounted to 22 and the saponification number had increased by 16. The oxide was sulfited at 70°-80° C. by the addition of 9% sodium disulfite and then adjusted to pH 6.5 with ammonia. An oil having an opal colour at 20° C. was obtained.

Chrome tanned and dyed cattle hide, retanned with anionic polymer tanning agent, with a fold thickness of 0.8 to 1.0 mm, was liquored at 50° C. in 150% float for 60 minutes with 10% of the product so obtained (relative to the shaved weight). After drying conventionally and finishing, a very soft flexible clothing and furniture leather having a very even mill grain and a high degree of fade resistance was obtained.

EXAMPLE 9

A mixture of 700 g of reaction product from Example 2 and 300 g of a hydrocarbon mixture of chain length $C_{10}$ to $C_{30}$ (acid number=3 and iodine number=56.1) was epoxidized with hydrogen peroxide in the presence of formic acid using a known process (see Houben-Weyl, volume 14/2, page 548). After separation of the aqueous phase, the washed and dried sample displayed the following characteristics: acid number=5.0; iodine number=14.5; epoxide oxygen=1.1%. The sulphation was carried out by careful introduction of 100 g of concentrated sulfuric acid at a maximum of 30° C. over a period of 2 hours. For purposes of subsequent reaction, this was stirred for a further hour at 30° C. and then adjusted to pH 5.5 with 30% sodium hydroxide solution. After washing with 100 g of 20% cooking salt solution a yellow emulsifiable oil was obtained, the pH value of which was adjusted to 6.5 to 7.0 in order to improve shelf stability.

White or coloured chrome tanned nappa leather from sheep hide was retanned with synthetic and/or polymer and/or resin tanning agents and liquored at 50° C. for 60 minutes with 200% float and 12% of the product obtained (relative to the fold weight). After conventional finishing soft nappa leather with a round hand, good pliability, little loose maculation, and high fade resistance was obtained.

COMPARATIVE EXAMPLE 1

560 g of the bone fat used in Example 1 with a solidification point of 25° C. was mixed as in Example 4 with 240 g of a hydrocarbon mixture with a chain length of $C_{10}$ to $C_{30}$ and 200 g of olein and then sulphonated. The sulfonate obtained after processing is non-homogeneous and not suitable for the production of liquid products that can be used as leather dubbing.

EXAMPLES 10 to 12

A fish oil with a strong sediment, a typical unplesant odour of train oil, a cloudiness at room temperature, and displaying the following characteristics, was used as a starting material:

Acid number: 21.7; iodine number: 161; Saponification number: 184; clarity point: not clear up to 100° C.

This product was converted as in Example 1 so that 5, 10 and 15%-wt of propoxylgroups were contained in the end product:

| Example | PO content (% wt) | Acid number | OH number | Iodine number | Saponification number | Appearance 20° C. | Appearance 10° C. | Odour |
|---|---|---|---|---|---|---|---|---|
| 10 | 5 | 0.39 | 62.4 | 152 | 174 | slightly cloudy thin oil | | slight, of train oil |
| 11 | 0 | 0.33 | 76.1 | 138 | 163 | clear thin oil | clear | scarcely any train oil odour |
| 2 | 15 | 0.36 | 82.6 | 124 | 153 | clear thin oil | clear | scarcely any train oil odour |

EXAMPLES 13–18

800 g (750 g) of propoxylated fish oil as in Examples 10 to 12 were accommodated in a controlling temperature sulphation column equipped with an anchor stirrer and a dropping funnel. 160 g (225 g) 97% sulfuric acid at a temperature of 32° C. was added drop by drop from the dropping funnel for 5 hours during intense agitation. Stirring was continued at 32° for a further hour to allow the reaction to settle down. The pH value of the resulting emulsion was adjusted to 6.8 by the addition of 30% sodium hydroxide solution whereupon the temperature rose to approximately 70° C. The separation into crude sulphonate and salt water resulted from the emulsion standing at approximately 70° C. The aqueous phase was removed and the sulphonate was adjusted to pH 8.3 with 45% sodium hydroxide solution.

| Example | Prop. fish oil from Example | 97% $H_2SO_4$ (% wt) | org $SO_3$ % wt | Appearance 20° C. | Water Content % wt |
|---|---|---|---|---|---|
| 13 | 10 | 20 | 3,5 | clear oil | 22 |
| 14 | 10 | 30 | 5,0 | cloudy oil | 22,7 |
| 15 | 11 | 20 | 3,4 | clear oil | 20,7 |
| 16 | 11 | 30 | 4,9 | clear oil | 21,2 |
| 17 | 12 | 20 | 3,5 | clear oil | 20,1 |
| 18 | 12 | 30 | 4,7 | clear oil | 20,3 |

Aroma assessment of products from Examples 13–18 revealed a scarcely perceptible odour of train oil at 20% $H_2SO_4$.

Odour of train oil at 30% $H_2SO_4$ could not be detected.

EXAMPLE 19

A chrome tanned upper leather retanned with an anionic polymer tanning agent was liquored at 50° C. in 150% float for one hour with 10%-wt (relative to the fold weight) of a clear mixture consisting of 50%-wt sulphonate from Example 18, 35%-wt white oil, 2% emulsifier, and 13%-wt water. After drying and finishing this resulted in a very soft and sweet smelling furniture leather.

COMPARATIVE EXAMPLE 2

The fish oil used in Examples 10 to 12 was sulphonated and processed without being previously converted with propylene oxide according to Examples 13 to 18, using 97% sulfuric acid:

| Quantity of 97% $H_2SO_4$ (% wt) | Organic $SO_3$ (% wt) | Water Content (% wt) | Appearance at 20° C. |
|---|---|---|---|
| 20 | 4,3 | 20,3 | cloudy oil |
| 30 | 4,9 | 19,9 | " |

Odour: a distinct odour of train oil.

The mixture as in Example 19 results in no clear leather dubbing.

We claim:

1. A process for the preparation of a derivative of a natural fat or oil which is liquid or free-flowing at room temperature, which comprises reacting a 1,2-epoxide at elevated temperature and in the presence of a basic catalyst with (a) a fat that is solid at room temperature, (b) a fat which contains solid fractions, or (c) with a mixture of at least one of (a) and (b) with a free fatty acid or with at least one of a mono- or di-glyceride, and sulphating the product of such reaction.

2. The product produced by the process of claim 1.

3. A process according to claim 1, wherein prior to sulphation the product is epoxidized.

4. A process according to claim 1, wherein the reaction with the 1,2-epoxide is effected at 150° to 170° C.

5. A process according to claim 1, wherein the 1,2-epoxide is employed in 5 to 100% of the weight of the material with which it is reacted.

6. A process according to claim 1, wherein the 1,2-epoxide is at least one of ethylene oxide, propylene oxide, butylene oxide, styrene oxide, 1,2-epoxy butadiene and 1,2-epoxy cyclohexene.

7. A process according to claim 1, wherein the 1,2-epoxide is at least one of propylene oxide and ethylene oxide.

8. A process according to claim 1, wherein the basic catalyst is at least one of potassium hydroxide, sodium hydroxide, sodium methylate and an alkaline salt of a fatty acid.

9. A process according to claim 1, wherein the sulphation is effected in the presence of at least one of an unsaturated hydrocarbon and an unsaturated fatty acid with concentrated sulfuric acid or sodium disulfite and atmospheric oxygen, and the reaction products so obtained are neutralized.

10. A process according to claim 1, wherein the material which is reacted with the 1,2-epoxide is a solid fat or oil with a turbidity point above the turbidity point of lard oil.

11. A process according to claim 1, wherein the reaction with the 1,2-epoxide is carried out at a pressure of 1 to 10 bar.

12. A process according to claim 1, wherein the sulphation is effected with concentrated sulphuric acid in about 15 to 35% the weight of the product of the reaction with the 1,2-epoxide.

13. A process according to claim 1, wherein the sulphation is effected at 20° to 50° C. with an $SO_3$/air mixture having a content of up to 8%-volume $SO_3$.

* * * * *